US012655076B2

(12) United States Patent (10) Patent No.: US 12,655,076 B2
Ha et al. (45) Date of Patent: Jun. 16, 2026

(54) REACTION APPARATUS AND PRODUCTION PROCESS FOR OLEFIN PRODUCTION

(71) Applicant: SOGANG UNIVERSITY RESEARCH & BUSINESS DEVELOPMENT FOUNDATION, Seoul (KR)

(72) Inventors: Kyoung-Su Ha, Seoul (KR); Won Ho Jung, Seoul (KR); Juchan Kim, Seoul (KR); Jinwon Lee, Seoul (KR)

(73) Assignee: SOGANG UNIVERSITY RESEARCH & BUSINESS DEVELOPMENT FOUNDATION, Seoul (KR)

( * ) Notice: Subject to any disclaimer, the term of this patent is extended or adjusted under 35 U.S.C. 154(b) by 275 days.

(21) Appl. No.: 18/703,665

(22) PCT Filed: Oct. 24, 2022

(86) PCT No.: PCT/KR2022/016265
§ 371 (c)(1),
(2) Date: Apr. 22, 2024

(87) PCT Pub. No.: WO2023/068907
PCT Pub. Date: Apr. 27, 2023

(65) Prior Publication Data
US 2024/0417343 A1 Dec. 19, 2024

(30) Foreign Application Priority Data
Oct. 22, 2021 (KR) ........................ 10-2021-0142084

(51) Int. Cl.
*C07C 2/80* (2006.01)
*B01J 8/18* (2006.01)
(Continued)

(52) U.S. Cl.
CPC ............... *C07C 2/80* (2013.01); *B01J 8/1827* (2013.01); *B01J 8/26* (2013.01); *B01J 8/42* (2013.01);
(Continued)

(58) Field of Classification Search
CPC ....... C07C 2/80; C07C 2521/08; C07C 5/333; C07C 1/02; C07C 2/74; C07C 11/04;
(Continued)

(56) References Cited

U.S. PATENT DOCUMENTS 4,814,534 A * 3/1989 Devries ..................... C07C 2/00
585/407
2016/0362351 A1* 12/2016 Nagaki .................. B01J 23/745
(Continued)

FOREIGN PATENT DOCUMENTS

AU 655469 12/1994
JP 03-220137 9/1991
(Continued)

OTHER PUBLICATIONS

International Search Report mailed Feb. 16, 2023 in corresponding PCT/KR2022/016265, 4 pages.
(Continued)

*Primary Examiner* — Prem C Singh
*Assistant Examiner* — Francis C Campanell
(74) *Attorney, Agent, or Firm* — HOVEY WILLIAMS LLP

(57) ABSTRACT

According to an embodiment of the present invention, there is provided a reaction apparatus for olefin production, including a feed separation unit that separates a methane feed and a light hydrocarbon feed from a supplied hydrocarbon feed; an ethane cracking unit that receives the light hydrocarbon feed from the feed separation unit and performs an ethane cracking process to produce an olefin product; and
(Continued)

a dielectric barrier reaction unit that receives the methane feed from the feed separation unit and generates a saturated hydrocarbon feed through plasma reaction, in which the saturated hydrocarbon feed is supplied into the ethane cracking unit, and an olefin product is produced from the supplied saturated hydrocarbon feed through an ethane cracking process.

10 Claims, 4 Drawing Sheets

(51) Int. Cl.

| | |
|---|---|
| *B01J 8/26* | (2006.01) |
| *B01J 8/42* | (2006.01) |
| *B01J 21/04* | (2006.01) |
| *B01J 21/06* | (2006.01) |
| *B01J 21/08* | (2006.01) |
| *B01J 23/02* | (2006.01) |
| *B01J 23/42* | (2006.01) |
| *B01J 23/46* | (2006.01) |
| *B01J 23/755* | (2006.01) |
| *B01J 31/02* | (2006.01) |

(52) U.S. Cl.
CPC ............ *B01J 21/04* (2013.01); *B01J 21/063* (2013.01); *B01J 21/08* (2013.01); *B01J 23/02* (2013.01); *B01J 23/42* (2013.01); *B01J 23/462* (2013.01); *B01J 23/755* (2013.01); *B01J 31/0217* (2013.01); *B01J 2231/005* (2013.01); *C07C 2521/08* (2013.01)

(58) Field of Classification Search
CPC ....... C07C 2521/04; B01J 8/1827; B01J 8/26; B01J 8/42; B01J 21/04; B01J 21/063; B01J 21/08; B01J 23/02; B01J 23/42; B01J 23/462; B01J 23/755; B01J 31/0217; B01J 2231/005; B01J 19/088; B01J 19/08; B01J 38/04; C07B 61/00; H05H 1/24; H05H 1/2406; Y02P 20/584
USPC ......................................................... 585/324
See application file for complete search history.

(56) References Cited

U.S. PATENT DOCUMENTS

| | | |
|---|---|---|
| 2020/0129952 A1 | 4/2020 | Ha et al. |
| 2020/0255750 A1 | 8/2020 | Fickel et al. |

FOREIGN PATENT DOCUMENTS

| | | |
|---|---|---|
| JP | 05-155785 | 6/1993 |
| KR | 10-2015-0098129 | 8/2015 |
| KR | 10-2020-0046834 | 5/2020 |

OTHER PUBLICATIONS

Machine Translation of KR20150098129, 34 pages.
Machine Translation of JP03220137, 10 pages.

\* cited by examiner

[FIG. 1]
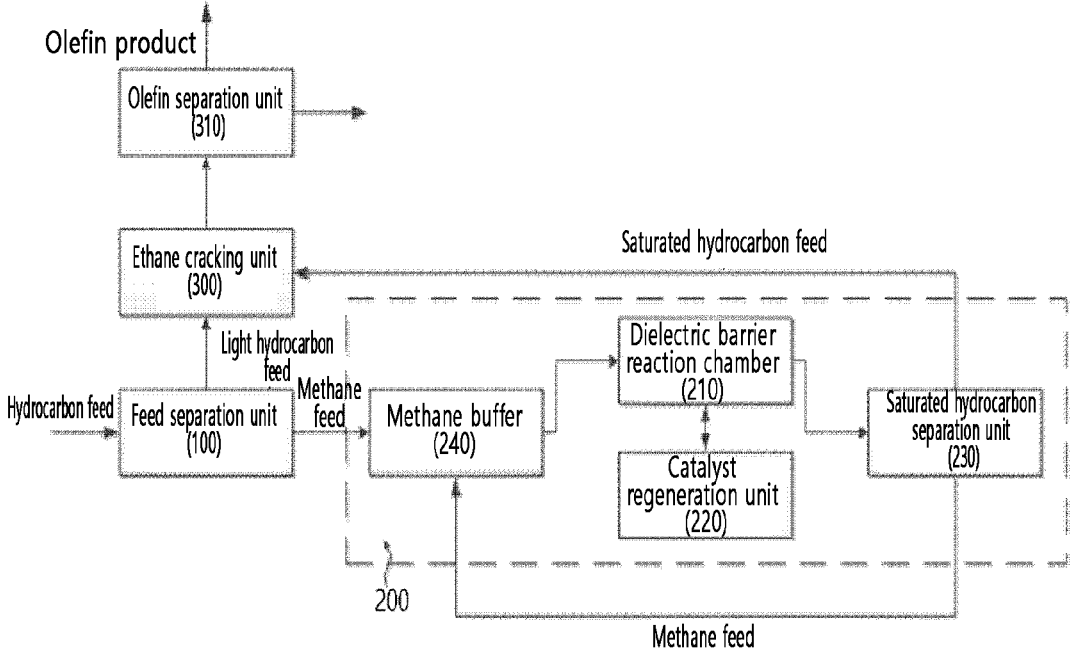
[FIG. 2]

[FIG. 3]

[FIG. 4]
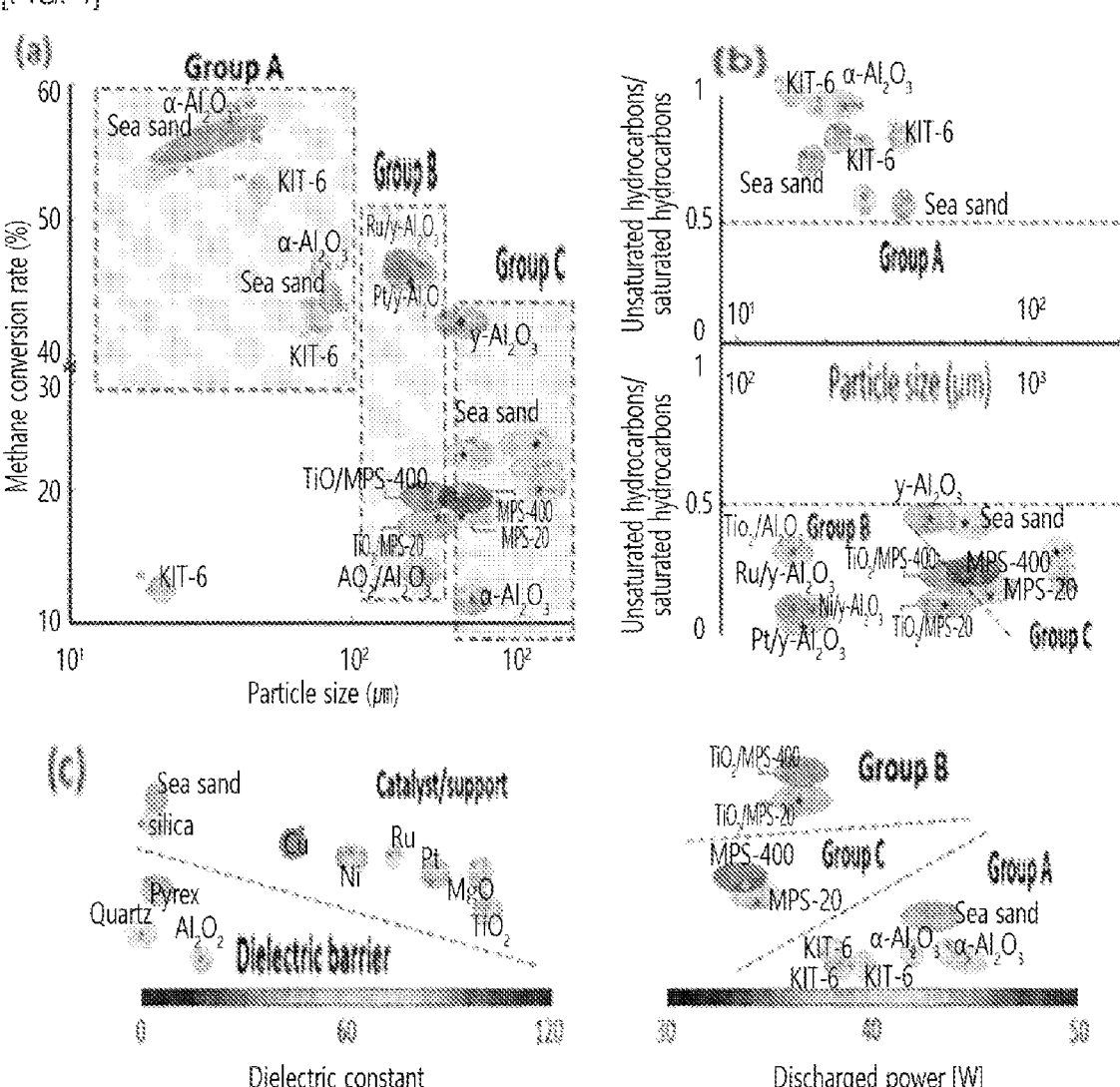

[FIG. 5]
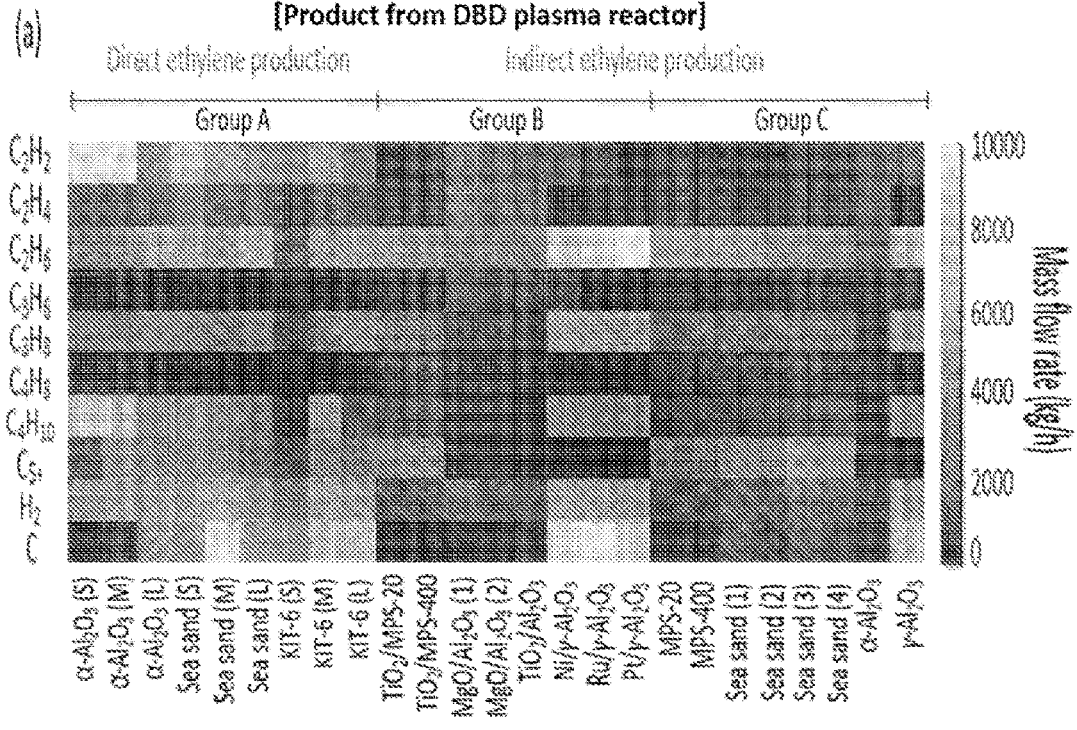
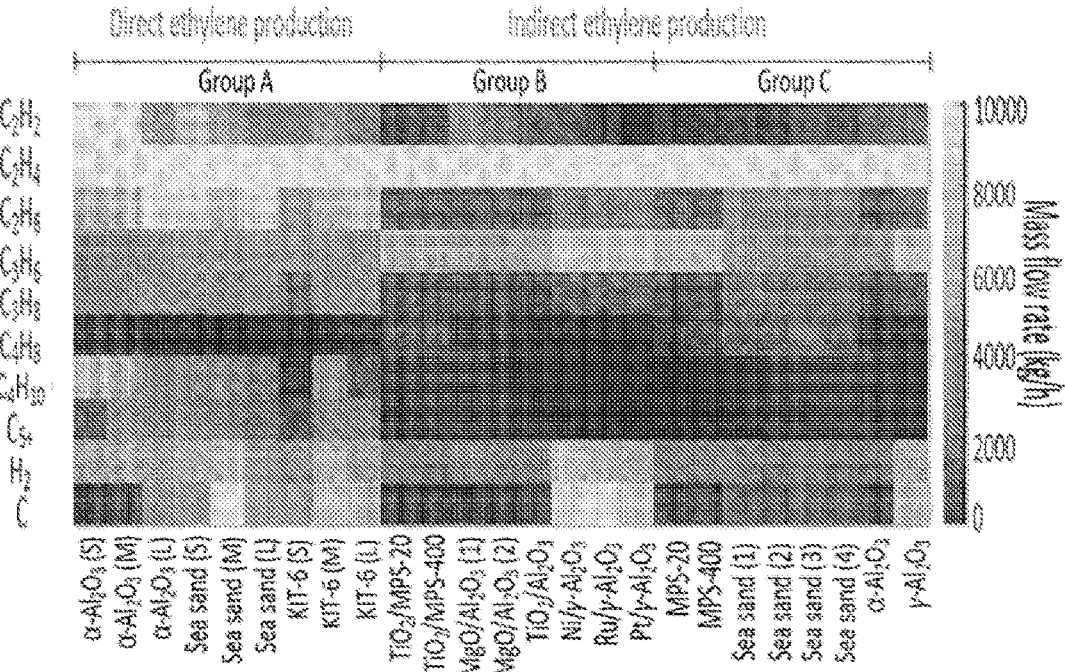

REACTION APPARATUS AND PRODUCTION PROCESS FOR OLEFIN PRODUCTION

RELATED APPLICATIONS

This application claims priority to PCT International Patent Application No. PCT/KR2022/016265, filed Oct. 24, 2022, which claims to Korean Application No. 10-2021-0142084, filed Oct. 22, 2021. Each of these applications is hereby incorporated by reference in their respective entireties.

TECHNICAL FIELD

The present invention relates to a production apparatus and production process for producing olefins from a carbon compound feed such as shale gas using an ethane cracking process and a plasma cracking process.

BACKGROUND ART

Light olefins, referring to ethylene, propylene, butene, and the like, are some of the most important products in petrochemicals, and are mainly produced by pyrolysis or fluidized catalytic cracking (FCC) of naphtha. However, because of the recent depletion of petroleum resources and high petroleum prices, a number of attempts have been made to produce light olefins, a petrochemical base oil, from resources (coal, natural gas, and the like) that can replace petroleum.

Meanwhile, shale gas, which has recently attracted attention, generally consists of $CH_4$ (80-90% v/v) and other light alkanes (for example, $C_2H_6$ and $C_3H_8$). As with existing petroleum resources, various attempts are being made to produce light olefins from shale gas.

Currently commonly used processes are an ethane cracking process or a methane reforming process. However, these processes still have a number of problems, such as high-temperature operation and catalyst deactivation by coke generation, and the industrial use thereof is limited.

In order to industrially generate olefins from light hydrocarbon feeds, not only olefin production yield and selectivity but also the cost required to generate the same amount of olefins is greatly important. From this perspective, the existing ethane cracking process or methane reforming process is advantageous in terms of selectivity for olefin production, but has the disadvantage of poor industrial feasibility.

Therefore, extensive research and development is still needed regarding technology for industrially generating olefins from light hydrocarbon feeds.

DISCLOSURE

Technical Problem

An object of the present invention is to produce olefins from a hydrocarbon feed at a high yield, a high selectivity and low cost.

Technical Solution

According to an embodiment of the present invention, there is provided a reaction apparatus for olefin production, including a feed separation unit that separates a methane feed and a light hydrocarbon feed from a supplied hydrocarbon feed; an ethane cracking unit that receives the light hydrocarbon feed from the feed separation unit and performs an ethane cracking process to produce an olefin product; and a dielectric barrier reaction unit that receives the methane feed from the feed separation unit and generates a saturated hydrocarbon feed through plasma reaction, in which the saturated hydrocarbon feed is supplied into the ethane cracking unit, and an olefin product is produced from the supplied saturated hydrocarbon feed through an ethane cracking process.

According to an embodiment of the present invention, at least one or more catalyst compounds selected from the group consisting of $TiO_2$, mercaptopropyl-functionalized silica (MPS), MgO, $Al_2O_3$, nickel (Ni), ruthenium (Ru), platinum (Pt), and crystalline silica ($SiO_2$) are provided in the dielectric barrier reaction unit, but the type of catalyst compound is not limited to the examples described above. There is provided a reaction apparatus for olefin production, in which the catalyst compound promotes generation of radicals from the methane feed and generation of the saturated hydrocarbon feed through a bonding reaction between radicals.

According to an embodiment of the present invention, there is provided a reaction apparatus for olefin production, in which a catalyst regeneration unit for regenerating the catalyst compound is further provided in the dielectric barrier reaction unit.

According to an embodiment of the present invention, there is provided a reaction apparatus for olefin production, in which the dielectric barrier reaction unit further includes a saturated hydrocarbon separation unit that separates methane ($CH_4$) from the generated saturated hydrocarbon feed, and methane separated in the saturated hydrocarbon separation unit is supplied again for plasma reaction for generating a saturated hydrocarbon feed.

According to an embodiment of the present invention, there is provided a reaction apparatus for olefin production, in which a plurality of dielectric barrier reaction chambers is provided in the dielectric barrier reaction unit.

According to an embodiment of the present invention, there is provided a reaction apparatus for olefin production, in which the olefin product includes ethylene and propylene.

According to an embodiment of the present invention, there is provided an olefin production process, including a first step of separating a methane feed and a light hydrocarbon feed from a hydrocarbon feed supplied in a feed separation unit; a 2A step of supplying the light hydrocarbon feed into an ethane cracking unit and performing an ethane cracking process to produce an olefin product; a 2B step of supplying the methane feed into a dielectric barrier reaction unit and producing a saturated hydrocarbon feed through plasma reaction; and a third step of supplying the saturated hydrocarbon feed into the ethane cracking unit and performing an ethane cracking process.

According to an embodiment of the present invention, there is provided an olefin production process, in which methane ($CH_4$) is separated from the saturated hydrocarbon feed generated after the step 2B and supplied again for plasma reaction for generating a saturated hydrocarbon feed.

According to an embodiment of the present invention, there is provided an olefin production process, in which a catalyst compound is provided inside the dielectric barrier reaction unit, and a catalyst regeneration step of regenerating the catalyst compound after plasma reaction is further performed.

According to an embodiment of the present invention, there is provided an olefin production process, in which at least one or more catalyst compounds selected from the group consisting of $TiO_2$, mercaptopropyl-functionalized silica (MPS), MgO, $Al_2O_3$, nickel (Ni), ruthenium (Ru), platinum (Pt), and crystalline silica ($SiO_2$) are provided in the dielectric barrier reaction unit, but the type of catalyst compound is not limited to the examples described above. The catalyst compound promotes generation of radicals from the methane feed and generation of the saturated hydrocarbon feed through a bonding reaction between radicals.

Advantageous Effects

According to an embodiment of the present invention, olefins can be produced from a hydrocarbon feed at a high yield, a high selectivity, and low cost.

According to an embodiment of the present invention, olefins can be produced from a hydrocarbon feed with less energy compared to existing processes.

BRIEF DESCRIPTION OF DRAWINGS

FIG. 1 is a block diagram illustrating a reaction process for olefin production according to an embodiment of the present invention;

FIG. 2 is a block diagram illustrating a reaction process for olefin production according to another embodiment of the present invention;

FIG. 3 illustrates a dielectric barrier reactor according to an embodiment of the present invention;

FIG. 4 illustrates the results of analyzing the methane conversion rate and generated unsaturated hydrocarbon/saturated hydrocarbon ratio when catalyst compounds according to the Comparative Example and the Examples of the present invention are used; and FIG. 5 illustrates the results of analyzing the generated hydrocarbon composition when catalyst compounds according to the Comparative Example and the Examples of the present invention are used.

DETAILED DESCRIPTION OF THE INVENTION

The present invention can be subject to various changes and have various forms, and specific embodiments will be illustrated in the drawings and described in detail in the text. This is not intended to limit the present invention to a specific disclosed form, but should be understood to include all changes, equivalents, and substitutes included in the spirit and technical scope of the present invention.

In the reaction apparatus and process for olefin production according to an embodiment of the present invention, two processes (ethane cracking and plasma decomposition) for decomposing a light hydrocarbon feed having 1 to 5 carbon atoms are organically combined, and thus the yield of olefins produced from a light hydrocarbon feed is excellent and the economic feasibility of olefin production is also excellent.

FIG. 1 is a block diagram illustrating the reaction process for olefin production according to an embodiment of the present invention.

Referring to FIG. 1, the reaction apparatus/process for olefin production according to an embodiment of the present invention includes a feed separation unit 100 that separates a methane feed and a light hydrocarbon feed from a supplied hydrocarbon feed; an ethane cracking unit 300 that receives the light hydrocarbon feed from the feed separation unit 100 and performs an ethane cracking process to produce an olefin product; and a dielectric barrier reaction unit 200 that receives the methane feed from the feed separation unit 100 and generates a saturated hydrocarbon feed through plasma reaction. The saturated hydrocarbon feed is supplied into the ethane cracking unit 300, and an olefin product is produced from the supplied saturated hydrocarbon feed through an ethane cracking process.

The feed separator 100 may purity/separate the hydrocarbon feed introduced into the process. Specifically, the hydrocarbon feed introduced into the feed separation unit 100 may be separated into a light hydrocarbon feed and a methane feed.

The hydrocarbon feed introduced into the feed separation unit 100 may be a mixture having a high content of alkanes, alkenes, and alkynes having 1 to 5 carbon atoms. The hydrocarbon feed may be, for example, shale gas. Shale gas may be, for example, a mixed composition having contents of methane ($CH_4$), ethane ($C_2H_6$) and propane ($C_3H_8$) of 80 mol %, 10 mol % and 5 mol %, respectively. In some cases, the hydrocarbon feed may contain methane ($CH_4$) and the like generated as by-products of other petrochemical processes.

The feed separation unit 100 may remove impurities contained in the supplied hydrocarbon feed. The feed separation unit 100 may remove, for example, impurities such as carbon dioxide ($CO_2$) and hydrogen sulfide ($H_2S$) contained in the hydrocarbon feed. In order to remove the above-mentioned impurities, the feed separation unit 100 may be provided with an aqueous amine solution tank, dust collection equipment, desulfurization equipment, and the like. However, the method for removing impurities is not particularly limited, and any means that can generally be used to remove impurities in petrochemical processes may be used. If necessary, a process of separating cycloalkanes, aromatic hydrocarbons, and the like that are unnecessary for subsequent processes may be performed in the feed separation unit 100.

The methane feed separated and generated in the feed separation unit 100 may be a mixture having a high methane content of 50% or more compared to the contents of other components. The light hydrocarbon feed may be a mixture containing hydrocarbons having 2 or 3 carbon atoms at a content of 50% or more.

As described above, the feed separation unit 100 may use methods such as distillation and pressure swing adsorption (PSA) to separate/produce a methane feed and a light hydrocarbon feed. However, in addition to the above-described methods, any method that can separate methane and hydrocarbons having 2 or 3 carbon atoms may be employed without limitation.

The methane feed separated in the feed separation unit 100 may be supplied into the dielectric barrier reaction unit 200.

The dielectric barrier reaction unit 200 receives the methane feed and generates a saturated hydrocarbon feed through plasma reaction. The dielectric barrier reaction unit 200 may specifically use a dielectric barrier discharge reaction. The supplied methane feed reacts with plasma in the above-described dielectric barrier discharge reaction to generate radicals such as $CH_3$ radicals and $CH_2$ radicals, and the generated radicals react with each other or with methane ($CH_4$) that has not yet reacted. A saturated hydrocarbon feed containing compounds such as ethane ($C_2H_6$) and propane ($C_3H_8$) may be generated through the radical reaction.

The dielectric barrier reaction unit 200 is different from a methane conversion reaction using conventional dielectric barrier discharge in that a saturated hydrocarbon feed is produced from a methane feed. Among the conventional $CH_4$ conversion methods using DBD plasma, the most actively researched field is the dry reforming reaction of $CH_4$ (DRM) with $CO_2$ to obtain syngas or liquid products. However, this reaction process has several disadvantages, such as relatively high temperature conditions (about 673 K to about 773 K) and a high coke formation rate. In the DBD plasma reaction conducted in the dielectric barrier reaction unit 200 of the present invention, HCs including olefins (unsaturated), paraffins (saturated), and hydrogen are mainly generated by non-oxidative conversion of methane. The composition of the material generated at this time may vary depending on the type and composition of the catalyst compound provided in the dielectric barrier reaction unit 200, and the amount and supply pattern of energy supplied.

Looking in more detail at the saturated hydrocarbon feed generated in the dielectric barrier reaction unit 200, the saturated hydrocarbon feed contains saturated hydrocarbons (C2, C3, C4, C5+). A saturated hydrocarbon feed having the composition described above leads to the formation of a greater amount of ethylene and propylene when supplied into the ethane cracking unit.

The dielectric barrier reaction unit 200 may include various types of reactors as well as a shell-and-tube type reactor. Any reactor type is possible as long as the reactor can be manufactured with a dielectric barrier material, an electrode, and an electric circuit to generate DBD plasma at an appropriate discharged power level.

The dielectric barrier reaction unit 200 may be provided with a catalyst compound that helps radicals generated by plasma reaction to form saturated hydrocarbons. The catalyst compound described above may be at least one or more materials selected from the group consisting of $TiO_2$, mercaptopropyl-functionalized silica (MPS), MgO, $Al_2O_3$, nickel (Ni), ruthenium (Ru), platinum (Pt), and crystalline silica ($SiO_2$). However, the type of catalyst compound is not limited to the above examples. The catalyst compound may promote the generation of radicals from a methane feed and the generation of a saturated hydrocarbon feed through a bonding reaction between radicals. Since the composition of the generated material may change depending on the type of catalyst compound provided in the dielectric barrier reaction unit 200, it is important to use an appropriate catalyst compound. Detailed analysis of changes in product composition depending on the type of catalyst compound will be described later.

The saturated hydrocarbon feed produced in the dielectric barrier reaction unit 200 may be supplied into the ethane cracking unit 300.

The ethane cracking unit 300 performs an ethane cracking process on the light hydrocarbon feed supplied from the feed separation unit 100 and the saturated hydrocarbon feed supplied from the dielectric barrier reaction unit 200 to produce an olefin product. At this time, as described above, since the ethane cracking unit 300 further performs a cracking process on the saturated hydrocarbon feed supplied from the dielectric barrier reaction unit 200, the olefin production yield may be greatly improved.

A tubular reactor may be used in the ethane cracking unit 300. In a tubular reactor, the residence time of the feed gas in the reactor may determine the production distribution. When the residence time of the reactants in the ethane cracking unit 300 is too short, the reaction may not sufficiently take place and the olefin yield may decrease. When the residence time is too long, the $CH_4$ selectivity is high and the olefin yield may be low. In the present invention, since the existing light hydrocarbon feed and the saturated hydrocarbon feed generated in the dielectric barrier reaction unit

200 are simultaneously supplied into the ethane cracking unit, the proportions of C4 and C5+ in the feed increase. The residence time of the reactants in the combined ethylene production technology is shorter than that in conventional ECC. Accordingly, the amount of olefins including ethylene, propylene, and butylene in the product greatly increases.

As described above, according to an embodiment of the present invention, a dielectric barrier reaction unit and an ethane cracking unit are organically combined to process a hydrocarbon feed, and thus a greater amount of olefin compounds can be produced from the hydrocarbon feed.

In addition, according to an embodiment of the present invention, a reaction process for olefin production using the above-described reaction apparatus can be performed. According to an embodiment of the present invention, an olefin production process may be provided, which includes a first step of separating a methane feed and a light hydrocarbon feed from a hydrocarbon feed supplied in a feed separation unit; a 2A step of supplying the light hydrocarbon feed into an ethane cracking unit and performing an ethane cracking process to produce an olefin product; a 2B step of supplying the methane feed into a dielectric barrier reaction unit and producing a saturated hydrocarbon feed through plasma reaction; and a third step of supplying the saturated hydrocarbon feed into the ethane cracking unit and performing an ethane cracking process.

The reaction apparatus/process for olefin production of the present invention may further include various additional configurations to achieve the purpose of improving the olefin production efficiency and reducing the process cost.

FIG. 2 is a block diagram illustrating the reaction process for olefin production according to another embodiment of the present invention.

Referring to FIG. 2, the dielectric barrier reaction unit 200 further includes a dielectric barrier reaction chamber 210, a catalyst regeneration unit 220, a saturated hydrocarbon separation unit 230, and a methane buffer 240, and an olefin separation unit 310 is further provided at the rear of the ethane cracking unit 300.

The dielectric barrier reaction chamber 210 refers to a reactor in which the plasma reaction according to dielectric barrier discharge (DBD) is conducted. The dielectric barrier reaction chamber 210, which is a reactor, may be provided with a dielectric barrier material, an electrode, and an electric circuit to generate DBD plasma at an appropriate discharged power level. The dielectric barrier reaction chamber 210 including the above-described members may be in various forms such as a tubular reactor as previously discussed as well as a shell-and-tube reactor, a multiple-rod reactor, and a multiple stacked cell-type reactor.

A plurality of dielectric barrier reaction chambers 210 may be provided. The plurality of dielectric barrier reaction chambers 210 may be operated simultaneously or alternatively. For example, when the amount of introduced methane feed is large, the dielectric barrier reaction chambers 210 may be operated simultaneously to increase the methane feed throughput per hour. In some cases, the plurality of dielectric barrier reaction chambers 210 may be operated alternatively. At this time, a catalyst regeneration process to regenerate the catalyst compound may be performed in the dielectric barrier reaction chamber 210 that is not in operation. After catalyst regeneration is completed, the dielectric barrier reaction chamber 210 that has been in operation may enter an idle state and catalyst regeneration may be performed. By alternatively operating the plurality of dielectric barrier reaction chambers 210 and performing catalyst regeneration in this way, the lifespan of catalyst compound may increase and a high level of reaction efficiency may be maintained even during continuous processes.

For the above-described catalyst regeneration operation, a catalyst regeneration unit 220 is provided.

The catalyst regeneration unit 220 may perform operations to remove coke adsorbed on the catalyst compound provided inside the dielectric barrier reaction chamber 210, and the like. The catalyst regeneration unit regenerates the catalyst compound by providing air flow inside the dielectric barrier reaction chamber 210. The catalyst regeneration unit 220 may be connected to a plurality of dielectric barrier reaction chambers 210, and when it is determined that regeneration of the catalyst compound is necessary, the plasma reaction of the methane feed in the dielectric barrier reaction chamber 210 may be stopped and catalyst regeneration may be performed by providing high-temperature air inside the dielectric barrier reaction chamber 210.

Next, the saturated hydrocarbon separation unit 230 may separate the saturated hydrocarbon feed generated after plasma reaction and the unreacted methane feed from the dielectric barrier reaction chamber 210. The saturated hydrocarbon separation unit 230 may perform the above-described separation through methods such as distillation and pressure swing adsorption (PSA).

The saturated hydrocarbon feed separated in the saturated hydrocarbon separation unit 230 mainly contains ethane and propane, and these are moved to the ethane cracking unit 300 as described above. In comparison, the methane feed separated in the saturated hydrocarbon separation unit 230 mainly contains methane, and is transferred to the methane buffer 240 to be used again in the dielectric barrier reaction. Therefore, even if the plasma reaction inside the dielectric barrier reaction chamber 210 is not complete, unreacted methane continues to be used in the plasma reaction, and the process yield of ultimately generating a saturated hydrocarbon feed from methane is excellent.

As described above, the methane buffer 240 functions to mix the methane feed separated and returned from the saturated hydrocarbon separation unit 230 and the methane feed provided from the feed separation unit 100. In some cases, a process of removing impurities that may affect the plasma reaction may be additionally performed in the methane buffer 240.

Next, an olefin separation unit 310 may be further provided at the rear of the ethane cracking unit 300. The olefin separation unit 310 may separate olefin compounds generated after the ethane cracking reaction from other compounds. For example, only ethylene and propylene may be utilized as olefin compounds, and other hydrocarbon compounds may be separated and utilized as energy sources.

The method for separating olefin compounds in the olefin separation unit 310 is not limited. For example, separation of olefin compounds may be performed through methods such as distillation and pressure swing adsorption (PSA).

Figure 3:
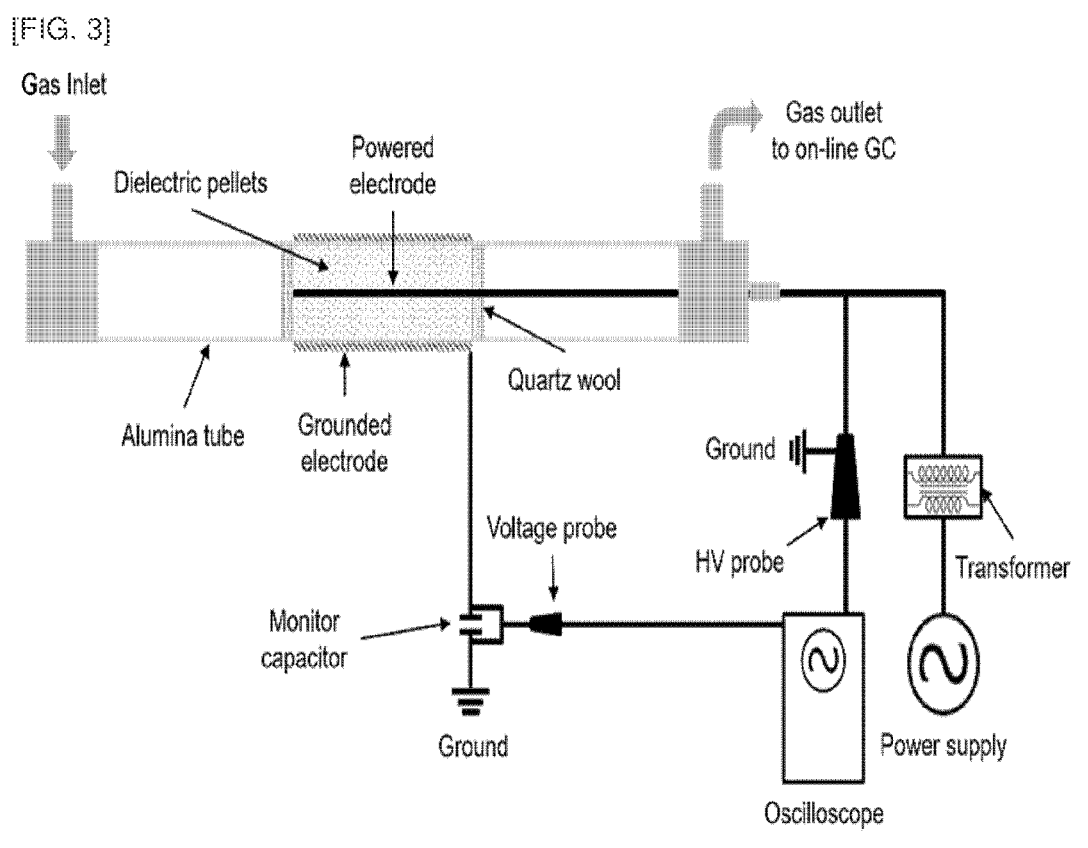

FIG. 3 illustrates the dielectric barrier reactor according to an embodiment of the present invention.

The dielectric barrier reactor according to FIG. 3 may include a powered electrode, a grounded electrode, dielectric pellets used as a dielectric barrier, a gas inlet, and a gas outlet. The powered electrode may be connected to a power supply unit that supplies power to generate plasma.

FIG. 3 illustrates a tubular reactor form in which the above-described members are provided in a pipe, and reactants and products flow in and out through the pipe. However, as previously discussed, the form of the dielectric barrier reactor is not limited to the above-mentioned examples. In addition to the above-mentioned forms, the dielectric barrier reactor may be provided in various forms such as a multiple-rod reactor and a multiple stacked cell-type reactor.

According to embodiments, the reaction in the dielectric barrier reactor may be conducted at room temperature and atmospheric pressure. In the Examples, a methane mixture ($CH_4:N_2=1:1$) having a space velocity (SV) of 750 $h^{-1}$ to 1500 $h^{-1}$ was injected into the reactor during the reaction, and the total reaction time was about 380 minutes. In the Examples, an alumina tube having an inner diameter of 6 mm and an outer diameter of 10 mm was used as a tubular reactor in the system. A stainless steel bar having a diameter of 3 mm and a length of 50 mm was used as the powered electrode, and a steel net wrapped with a steel wire was used as the grounded electrode. At this time, 150 mm of plasma bed was wrapped around the grounded electrode. The discharge gap between the inner surface of the alumina tube and the powered electrode was 1.5 mm. Therefore, the volume of this plasma emission region was fixed at 3.18 $cm^3$. In the Examples, the plasma bed was provided with as-prepared crystalline silica ($SiO_2$) particles having two particle size ranges (0.2 mm to 1.0 mm and 1.0 mm to 1.2 mm). A sinusoidal power supply device (0 V to 220 V, 60 Hz to 1000 Hz) was connected to a transformer (0 KV to 20 KV, 1000 Hz) to supply sinusoidal AC power to the plasma bed. The applied voltage and frequency were set to 15 kV (equivalent to 30 KV peak-to-peak voltage) and 1 kHz, respectively.

FIG. 4 illustrates the results of analyzing the methane conversion rate and generated unsaturated hydrocarbon/saturated hydrocarbon ratio when catalyst compounds according to the Comparative Example and the Examples of the present invention are used.

The composition distribution of the product in the dielectric barrier reaction unit is influenced by factors such as dielectric particle size, dielectric constant, catalyst particle size, and metal impregnation.

The catalyst particle size had the greatest influence on product distribution. As the catalyst particle size increased, the $CH_4$ conversion rate decreased (A of FIG. 4). When a catalyst having a particle size of 100 μm was used, the $CH_4$ conversion rate was about 40% to about 60%, and the ratio of unsaturated hydrocarbons to saturated hydrocarbons was higher than 0.5 as illustrated in B of FIG. 4. When the above-described catalyst was used, acetylene exhibited the highest yield and a small amount of ethylene was also generated.

Conversely, when the catalyst particle size was greater than 100 μm, the $CH_4$ conversion rate was relatively low (about 10% to about 50%). At this time, the ratio of unsaturated hydrocarbons to saturated hydrocarbons was less than 0.5. In this case, the yield of saturated hydrocarbons consisting mainly of $C_2H_6$, $C_3H_8$ and C4+ was high. This region includes both non-metallic dielectric particles and metal-impregnated dielectric catalysts having different dielectric properties.

In the present invention, dielectric catalyst species were classified into small non-metal dielectric particles (Group A) of the Comparative Example, large dielectric particles loaded with a metal or metal oxide (Group B) of Example, and large non-metal dielectric particles (Group C) of Example depending on the particle size and presence or absence of metal impregnation.

TABLE 1

| | Catalyst | $d_p$ [μm] | $X_{CH4}$ [%] | Unsat. HCs [%] | Sat. HCs [%] | $H_2$ [%] | V [kV] | f [kHz] |
|---|---|---|---|---|---|---|---|---|
| Group A (Comparative Example) | $\alpha$-Al$_2$O$_3$ (S) 1 | 25 | 54.8 | 53.5 | 46.5 | 59.00 | 15 | 1 |
| | $\alpha$-Al$_2$O$_3$ (M) 1 | 50 | 58.4 | 49.1 | 48.8 | 58.00 | 15 | 1 |
| | $\alpha$-Al$_2$O$_3$ (L) 1 | 100 | 46.4 | 27.5 | 53.8 | 50.00 | 15 | 1 |
| | Sea sand (S) 1 | 25 | 54.6 | 38.2 | 48.1 | 64 | 15 | 1 |
| | Sea sand (M) 1 | 50 | 57.2 | 22.2 | 42.1 | 65 | 15 | 1 |
| | Sea sand (L) 1 | 100 | 43.5 | 21.9 | 53.8 | 52 | 15 | 1 |
| | KIT-6 (S) 1 | 25 | 22.5 | 29.7 | 29.9 | 59 | 15 | 1 |
| | KIT-6 (M) 1 | 50 | 52.9 | 23.6 | 44.7 | 59.5 | 15 | 1 |
| | KIT-6 (L) 1 | 100 | 41.8 | 16.0 | 44.3 | 52 | 15 | 1 |
| Group B (Example) | TiO$_2$/MPS-20 2 | 350 | 18.63 | 15.1 | 83.8 | 48.60 | 15 | 1 |
| | TiO$_2$/MPS-400 2 | 350 | 19.96 | 16.7 | 83.1 | 46.63 | 15 | 1 |
| | MgO/Al$_2$O$_3$ (1) 3 | 250 | 23.0 | 68 | 32.0 | 51.58 | 6 | 3 |
| | MgO/Al$_2$O$_3$ (2) 3 | 500 | 16.2 | 55.7 | 44.3 | 52.04 | 6 | 3 |
| | TiO$_2$/Al$_2$O$_3$ 3 | 500 | 14.0 | 49.0 | 45.0 | 46.80 | 6 | 3 |
| | Ni/$\gamma$-Al$_2$O$_3$ 4 | 200 | 48.1 | 7.54 | 52.2 | 38.89 | 3, 3.2, 4 | 23 |
| | Ru/$\gamma$-Al$_2$O$_3$ 4 | 200 | 48.1 | 2.65 | 54.1 | 33.55 | 3, 3.2, 4 | 23 |
| | Pt/$\gamma$-Al$_2$O$_3$ 4 | 200 | 47 | 0 | 62.7 | 32.92 | 3, 3.2, 4 | 23 |
| Group C (Example) | MPS-20 2 | 350 | 18.59 | 17.6 | 79.3 | 49.62 | 15 | 1 |
| | MPS-400 2 | 350 | 20.61 | 16.4 | 78.1 | 46.09 | 15 | 1 |
| | Sea Sand (1) a | 600 | 24.97 | 18.99 | 60.48 | 41.92 | 15 | 1 |
| | Sea Sand (2) a | 1100 | 23.35 | 12.85 | 68.16 | 43.45 | 15 | 1 |
| | Sea Sand (3) a | 1100 | 16.57 | 15.59 | 64.98 | 39.94 | 15 | 1 |
| | Sea Sand (4) a | 1100 | 12.54 | 17.59 | 63.17 | 39.22 | 15 | 1 |
| | $\alpha$-Al$_2$O$_3$ 3 | 500 | 10.0 | 59.0 | 37.0 | 50.28 | 6 | 3 |
| | $\gamma$-Al$_2$O$_3$ 4 | 200 | 42.5 | 10.31 | 53.4 | 39.69 | 3, 3.2, 4 | 23 |

As can be seen from the figure, the proportion of unsaturated hydrocarbons generated after plasma reaction was high in the case of Group A of the Comparative Example, and the proportion of saturated hydrocarbons generated was high in the case of Group B and Group C of the Examples. Therefore, it can be seen that when the catalyst compounds of Group A are used, it is difficult to perform the ethane cracking process by supplying the saturated hydrocarbon feed generated after plasma reaction to the ethane cracking unit since the proportion of unsaturated hydrocarbons is high. In comparison, it can be seen that when the catalyst compounds of Group B and Group C of the Examples are used, the ethane cracking process is suitably performed by supplying the saturated hydrocarbon feed generated after plasma reaction to the ethane cracking unit since the proportion of saturated hydrocarbons is high.

In order to further validate the feasibility of commercialization, $CH_4$ conversion experiments were conducted using the catalyst compounds of each group. The dielectric constants of catalyst compound particles of the three groups are illustrated in C of FIG. 4.

The materials mainly used as dielectric barriers when dielectric barrier plasma reaction is conducted, are alumina, silica, and Pyrex tubes, which have dielectric constants of 9.8, 3.9, and 4.84, respectively. In general, the dielectric constants of metals or metal oxides are higher than those of alumina, silica, and Pyrex.

The discharged power in the dielectric barrier reaction unit was higher in Group A than in Group B and Group C. Therefore, when the catalyst compounds of Group B and Group C of the Examples are used, the reaction can be conducted with a relatively low power.

The distribution and heat map of products from the dielectric barrier reaction unit using DBD plasma reaction and the combined processes with the ethane cracking unit and the dielectric barrier reaction unit are illustrated in A and B of FIG. 5, respectively. Referring to A of FIG. 5, the $C_2H_2$ fraction generated after plasma reaction was the largest in Group A, the catalysts of the Comparative Example. In the Comparative Example, $C_2H_4$, $C_2H_6$, $C_4H_{10}$, and $H_2$ were produced in large quantities, whereas $C_3H_6$ and $C_4H_8$ were produced in small quantities. In general, the product distribution of Group A was very diverse unlike those of Groups B and C, and this implies that the product requires numerous rear-end separation processes.

The catalysts of Group B and Group C of the Examples showed similar product distributions. In Group B, there was a difference in the generation of $C_2H_4$ and coke deposits, and it was found that the catalytic functions of the metal oxides and metals contained in the catalyst compounds of Group B affected the plasma reaction. More specifically, dielectric catalysts impregnated with metals, such as Ni, Ru, and Pt, among the catalyst compounds of Group B can generate more saturated hydrocarbons than olefins by hydrogenation. The large amount of carbon deposited in the dielectric barrier reaction unit is considered to be caused by the high bed temperature. The $CH_4$ conversion speed was high because of the high catalytic activity of the metal-impregnated catalysts. On the other hand, metal-oxide-impregnated dielectric catalysts suppressed the formation of coke and increased the selectivity toward saturated hydrocarbons, but the $CH_4$ conversion speed was lower than that of metal-impregnated dielectric catalysts.

Next, in the case of a combined processes with the ethane cracking unit and the dielectric barrier reaction unit, as can be seen from B of FIG. 5, a large amount of ethylene was generated in all catalyst groups of the Examples and the Comparative Example through the ethane cracking process. The product distribution of Group A, catalysts of the Comparative Example, is still analyzed to be complex. However, the amount of $C_2H_4$ in Group A may be further increased by the hydrogenation of $C_2H_2$. In Groups B and C of the Examples, the amount of $C_3H_6$ generated significantly increased. In the case of using catalyst compounds of the Examples, the selectivity for other hydrocarbons except for $C_2H_4$ and $C_3H_6$ was very low because of the consumption of C4 and C5+ in the ethane cracking unit.

$C_2H_6$, $C_3H_8$, C4, and C5+ are mainly produced in the dielectric barrier reaction unit containing catalyst compounds of Group B and Group C of the Examples. When a pure $C_2H_6$ feed is supplied into the ethane cracking unit, a $C_2H_6$-$C_3H_8$ mixture is supplied, and naphtha is supplied, the reaction product compositions are as shown in the table below.

TABLE 2

| Composition (wt. %) | $C_2H_6$ feed | $C_2H_6$—$C_3H_8$ feed | Naphtha feed |
|---|---|---|---|
| H2 | 3.77 | 3.1 | 1.0 |
| CH4 | 3.90 | 8.5 | 16.6 |
| C2H2 | 0.43 | 0.1 | 0 |
| C2H4 | 47.40 | 44.1 | 30.8 |
| C2H6 | 39.48 | 26.5 | 4.0 |
| C3H6 | 0.50 | 9.9 | 13.9 |
| C3H8 | 0.15 | 4.2 | 0 |
| C4H6 | 0 | 0 | 4.5 |
| C4H8 | 0 | 0 | 5.0 |
| Aromatics | 0 | 0 | 24.2 |

As the proportion of $C_2H_6$ in the feed to the ethane cracking unit increased, the selectivity for ethylene increased, whereas the selectivity for by-products such as C4+ hydrocarbons converged to almost 0. Conversely, in a case where C5+ contained in naphtha was supplied, the $C_2H_4$ yield decreased, whereas the $C_3H_6$ and $C_4H_8$ yields increased.

In the existing ethane cracking process, the production yield of olefins including ethylene from shale gas containing $CH_4$, $C_2H_6$, and $C_3H_8$ was only about 20.8%. However, when the combined processes according to an embodiment of the present invention is used, the olefin production yield increases to about 24.5% to about 38.3%. in addition, in a case where 90% of the unreacted $CH_4$ is recycled in the dielectric barrier reaction unit, the olefin production yield increases to about 45.9% to about 60.4%.

Consequently, it means that the combined processes according to an embodiment of the present invention can sufficiently secure the yield and economic feasibility compared to the existing process.

In the above, the present invention has been described with reference to preferred embodiments, but those skilled in the art or those having ordinary knowledge in the art will understand that various modifications and changes can be made to the present invention without departing from the spirit and technical scope of the present invention as set forth in the claims to be described later.

Therefore, the technical scope of the present invention should not be limited to what is described in the detailed description of the specification, but should be defined by the claims.

The invention claimed is:

1. A reaction apparatus for olefin production, comprising:
a feed separation unit that separates a methane feed and a light hydrocarbon feed from a supplied hydrocarbon feed;
an ethane cracking unit that receives the light hydrocarbon feed from the feed separation unit and performs an ethane cracking process to produce an olefin product; and

12 a dielectric barrier reaction unit that receives the methane feed from the feed separation unit and generates a saturated hydrocarbon feed through plasma reaction, wherein
the saturated hydrocarbon feed is supplied into the ethane cracking unit, and an olefin product is produced from the supplied saturated hydrocarbon feed through an ethane cracking process.

2. The reaction apparatus for olefin production according to claim 1, wherein
at least one or more catalyst compounds selected from the group consisting of $TiO_2$, mercaptopropyl-functionalized silica (MPS), MgO, $Al_2O_3$, nickel (Ni), ruthenium (Ru), platinum (Pt), and crystalline silica ($SiO_2$) are provided in the dielectric barrier reaction unit, and
the catalyst compound promotes generation of radicals from the methane feed and generation of the saturated hydrocarbon feed through a bonding reaction between radicals.

3. The reaction apparatus for olefin production according to claim 2, wherein
a catalyst regeneration unit for regenerating the catalyst compound is further provided in the dielectric barrier reaction unit.

4. The reaction apparatus for olefin production according to claim 1, wherein
the dielectric barrier reaction unit further includes a saturated hydrocarbon separation unit that separates methane ($CH_4$) from the generated saturated hydrocarbon feed, and
methane separated in the saturated hydrocarbon separation unit is supplied again for plasma reaction for generating a saturated hydrocarbon feed.

5. The reaction apparatus for olefin production according to claim 1, wherein
a plurality of dielectric barrier reaction chambers is provided in the dielectric barrier reaction unit.

6. The reaction apparatus for olefin production according to claim 1, wherein
the olefin product includes ethylene and propylene.

7. An olefin production process comprising:
a first step of separating a methane feed and a light hydrocarbon feed from a hydrocarbon feed supplied in a feed separation unit;
a 2A step of supplying the light hydrocarbon feed into an ethane cracking unit and performing an ethane cracking process to produce an olefin product;
a 2B step of supplying the methane feed into a dielectric barrier reaction unit and producing a saturated hydrocarbon feed through plasma reaction; and
a third step of supplying the saturated hydrocarbon feed into the ethane cracking unit and performing an ethane cracking process.

8. The olefin production process according to claim 7, wherein
methane ($CH_4$) is separated from the saturated hydrocarbon feed generated after the step 2B and supplied again for plasma reaction for generating a saturated hydrocarbon feed.

9. The olefin production process according to claim 7, wherein
a catalyst compound is provided inside the dielectric barrier reaction unit, and
a catalyst regeneration step of regenerating the catalyst compound after plasma reaction is further performed.

10. The olefin production process according to claim 7, wherein at least one or more catalyst compounds selected from the group consisting of $TiO_2$, mercaptopropyl-functional-ized silica (MPS), MgO, $Al_2O_3$, nickel (Ni), ruthenium (Ru), platinum (Pt), and crystalline silica ($SiO_2$) are provided in the dielectric barrier reaction unit, and the catalyst compound promotes generation of radicals from the methane feed and generation of the saturated hydrocarbon feed through a bonding reaction between radicals.

* * * * *